(12) United States Patent
Spataro et al.

(10) Patent No.: US 11,338,114 B2
(45) Date of Patent: May 24, 2022

(54) MAGNETIC CATHETER SYSTEM AND METHODS

(71) Applicant: Becton, Dickinson and Company, Franklin Lakes, NJ (US)

(72) Inventors: Joseph Spataro, Cottonwood Heights, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 9 days.

(21) Appl. No.: 16/918,735

(22) Filed: Jul. 1, 2020

(65) Prior Publication Data

US 2021/0008349 A1 Jan. 14, 2021

Related U.S. Application Data

(60) Provisional application No. 62/872,128, filed on Jul. 9, 2019.

(51) Int. Cl.
*A61M 25/06* (2006.01)

(52) U.S. Cl.
CPC .... *A61M 25/0631* (2013.01); *A61M 25/0606* (2013.01); *A61M 25/0625* (2013.01); *A61M 2205/02* (2013.01)

(58) Field of Classification Search
CPC .......... A61M 25/0606; A61M 25/0618; A61M 25/0625; A61M 25/0631; A61M 25/0637; A61M 2205/02

See application file for complete search history.

(56) References Cited

U.S. PATENT DOCUMENTS

| | | | |
|---|---|---|---|
| 7,740,614 B2* | 6/2010 | Murashita ......... | A61M 25/0637 604/164.08 |
| 8,939,938 B2* | 1/2015 | Funamura ......... | A61M 25/0618 604/164.08 |
| 9,555,221 B2* | 1/2017 | Koehler ................ | A61M 5/329 |
| 10,548,522 B2* | 2/2020 | Akcay .............. | A61B 5/150992 |
| 2004/0225260 A1* | 11/2004 | Villa ................... | A61M 5/3273 604/164.01 |
| 2008/0086089 A1* | 4/2008 | Isaacson ............. | A61M 5/3273 604/164.08 |
| 2008/0103449 A1* | 5/2008 | Murashita ......... | A61M 25/0637 604/164.08 |
| 2020/0254195 A1* | 8/2020 | Nakagami ......... | A61M 25/0097 |

FOREIGN PATENT DOCUMENTS

| | | | | |
|---|---|---|---|---|
| EP | 0645159 | | 3/1995 | |
| EP | 0645159 A1 * | | 3/1995 | .......... A61M 5/3273 |
| JP | 2005270638 | | 10/2005 | |
| JP | 4661240 B2 * | | 3/2011 | ........ A61M 25/0618 |

(Continued)

*Primary Examiner* — Rebecca E Eisenberg
*Assistant Examiner* — Adam J. Cermak
(74) *Attorney, Agent, or Firm* — Kirton Mcconkie; Whitney Blair; Kevin Stinger (57) ABSTRACT

A catheter system may include a needle assembly coupled to a catheter adapter. The needle assembly may include a housing, an introducer needle, a distal opening, a first magnet, and a second magnet. In response to proximal withdrawal of the introducer needle, the first magnet may move towards the second magnet, which may block the distal opening and/or prevent blood from leaking out the distal opening.

20 Claims, 9 Drawing Sheets

(56) References Cited

FOREIGN PATENT DOCUMENTS

| JP | 2016007429 | 1/2016 | |
|----|------------|--------|---|
| WO | 2013/027355 | 2/2013 | |
| WO | WO-2013027355 A1 * | 2/2013 | ........ A61M 25/0618 |
| WO | WO-2015098590 A1 * | 7/2015 | ........ A61M 25/0618 |
| WO | WO-2016133138 A1 * | 8/2016 | ............ A61M 5/158 |
| WO | 2018/163028 | 9/2018 | |
| WO | WO-2018163028 A1 * | 9/2018 | ........ A61M 39/0613 |

\* cited by examiner

MAGNETIC CATHETER SYSTEM AND METHODS

RELATED APPLICATIONS

This application claims the benefit of U.S. Provisional Patent Application 62/872,128, filed Jul. 9, 2019 and entitled MAGNETIC CATHETER SYSTEM AND METHODS which is incorporated herein in its entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over a needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient. Once placement of the needle within the vasculature has been confirmed, the user may temporarily occlude flow in the vasculature and withdraw the needle, leaving the intravenous catheter in place for future blood withdrawal and/or fluid infusion.

When the needle is withdrawn from the intravenous catheter, clinician safety is a major concern. Not only is there a risk of needle-stick injury, the clinician wants to avoid any blood exposure from the needle. Competing for the clinician's desire for safety is a desire to maintain the intravenous catheter within the vasculature of the patient during withdrawal of the needle. Friction-based drag force as the needle is withdrawn from the intravenous catheter may lead to dislodgement of the catheter from the insertion site. Due to the friction-based drag force, the clinician may somewhat awkwardly hold the intravenous catheter in place while trying to withdraw the needle in a safe manner.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to catheter systems, as well as related devices and methods. In some embodiments, a catheter system may include a catheter adapter, which may include a distal end, a proximal end, and a wall forming a lumen. In some embodiments, the catheter system may include a catheter extending distally from the distal end of the catheter adapter. In some embodiments, the catheter may include a peripheral intravenous catheter ("PIVC"), a midline catheter, a peripherally inserted central catheter ("PICC"), or another suitable catheter.

In some embodiments, the catheter system may include a needle assembly coupled to the catheter adapter. In some embodiments, the needle assembly may include an introducer needle, which may include a distal tip and a bump feature. In some embodiments, the distal tip may be disposed distal to the catheter in a first position. In some embodiments, the first position may correspond to an insertion position, ready for insertion into vasculature of a patient.

In some embodiments, the proximal end of the introducer needle may be secured within a needle hub. In some embodiments, the needle hub may be proximate the housing. In some embodiments, the needle hub may include one or more grip features, which may facilitate movement of the needle hub in a proximal direction by a clinician to withdraw the introducer needle from the vasculature of the patient and the catheter.

In some embodiments, the needle assembly may include a housing, which may include a distal opening, a proximal opening, and a pathway extending between the distal opening and the proximal opening. In some embodiments, a diameter of the proximal opening may be less than an outer diameter of the bump feature. In some embodiments, the introducer needle may extend through the pathway.

In some embodiments, the housing may include a first portion, which may include a magnet extending there through. In some embodiments, the magnet may include a first magnetic pole and a second magnetic pole. In some embodiments, the magnet may include a permanent magnet. In some embodiments, the magnet may be oriented generally perpendicular to a longitudinal axis of the catheter system.

In some embodiments, the housing may include a second portion, which may include another magnet. In some embodiments, the other magnet may include a first magnetic pole and a second magnetic pole. In some embodiments, the other magnet may include a permanent magnet. In some embodiments, the second magnetic pole of the other magnet may be proximal to the first magnetic pole of the other magnet. In some embodiments, the other magnet may be oriented generally parallel to a longitudinal axis of the catheter system. In some embodiments, the magnet and/or the other magnet may be proximate or in communication with the pathway, which may increase a magnetic force between the magnet and the other magnet.

In some embodiments, the second magnetic pole of the magnet may be aligned with and repelled by the second magnetic pole of the other magnet. In some embodiments, the introducer needle may be disposed between the second magnetic pole of the magnet and the second magnetic pole of the other magnet. In some embodiments, the repulsion between the second magnetic pole of the magnet and the second magnetic pole of the other magnet may reduce a friction-based drag force on the introducer needle as the introducer needle is withdrawn. In some embodiments, because of the spacing and repulsion between the second magnetic pole of the magnet and the second magnetic pole of the other magnet, the second magnetic pole of the magnet and/or the second magnetic pole of the other magnet may be spaced apart from an outer surface of the introducer needle, which may reduce the friction-based drag force on the introducer needle as the introducer needle is withdrawn.

In some embodiments, the wall of the catheter adapter may include a slot. In some embodiments, the first magnetic pole of the magnet may be disposed within the slot, which may couple the needle assembly to the catheter adapter. In some embodiments, when the catheter adapter is coupled to the needle assembly via the other magnet disposed in the slot, a magnetic repelling force between the magnet and the other magnet may be at a high or peak value, which may simultaneously secure the catheter adapter and the needle assembly together and may reduce the friction-based drag force.

In some embodiments, the distal tip of the introducer needle may be configured to be withdrawn proximally from the first position to a second position in which the bump feature contacts the proximal opening. In some embodiments, the bump feature may be prevented from passing through the proximal opening due to the outer diameter of the bump feature.

In some embodiments, the distal tip of the introducer needle may be configured to be withdrawn proximally from the second position to a third position. In some embodiments, in response to withdrawing the distal tip of the introducer needle proximally from the second position to the third position, the second portion may slide proximally with respect to the first portion and the second magnetic pole of the magnet may be aligned with and attracted to the first magnetic pole of the other magnet such that the magnet moves inwardly towards the other magnet. In some embodiments, in response to the magnet moving inwardly towards the other magnet, the magnet may block the distal opening and/or prevent blood from leaking out the distal opening. In some embodiments, blocking the distal opening may prevent needle stick injury. In some embodiments, when the distal tip is disposed in the third position, a magnetic attraction force between the magnet and the other magnet may be at a high or peak value, which may facilitate securement of the distal tip within the housing.

In some embodiments, the other magnet may shield the distal tip within the housing when the distal tip is disposed in the third position, and may also act as a coupling component configured to couple the needle assembly to the catheter adapter when the distal tip is in the first position and/or the second position. In some embodiments, in response to withdrawing the distal tip of the introducer needle proximally from the second position to the third position, the second magnetic pole of the magnet may be aligned with and attracted to the first magnetic pole of the other magnet such that the magnet moves inwardly towards the other magnet and is removed from the slot. In some embodiments, in response to the other magnet being removed from the slot, the catheter adapter and the needle assembly may be uncoupled and/or the needle assembly may be removed from the catheter adapter.

In some embodiments, the magnet may be replaced with a temporary magnet. In some embodiments, the temporary magnet may include steel, iron, or another suitable material. In these and other embodiments, the first portion and the second portion may be integrally formed and may not slide with respect to each other. In some embodiments, the introducer needle may be disposed between the other magnet and the temporary magnet.

In some embodiments, the distal tip of the introducer needle may be configured to be withdrawn proximally from the first position to the second position. In some embodiments, in response to withdrawing the distal tip of the introducer needle proximally from the first position to the second position, the bump feature may contact the proximal opening of the housing, the distal tip may be disposed proximal to the temporary magnet and the other magnet, and the temporary magnet may move inwardly towards the other magnet to block the distal opening and/or prevent blood from leaking out the distal opening.

In some embodiments, the other magnet may include a permanent magnet, and the temporary magnet may be attracted to the permanent magnet. In some embodiments, the temporary magnet may contact and/or press lightly on the introducer needle when the distal tip is in the first position due to the attraction between the temporary magnet and the other magnet. In some embodiments, the other magnet may be spaced apart from the introducer needle when the distal tip is in the first position, which may reduce the friction-based drag force on the introducer needle as the introducer needle is withdrawn. In some embodiments, the other magnet may contact and/or press lightly on the introducer needle when the distal tip is in the first position.

In some embodiments, the temporary magnet may be disposed within the slot. In some embodiments, in response to withdrawing the distal tip of the introducer needle proximally from the first position to the second position, the temporary magnet may move inwardly towards the permanent magnet and may be removed from the slot. In some embodiments, in response to the temporary magnet being removed from the slot, the catheter adapter and the needle assembly may be uncoupled and/or the needle assembly may be removed from the catheter adapter.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
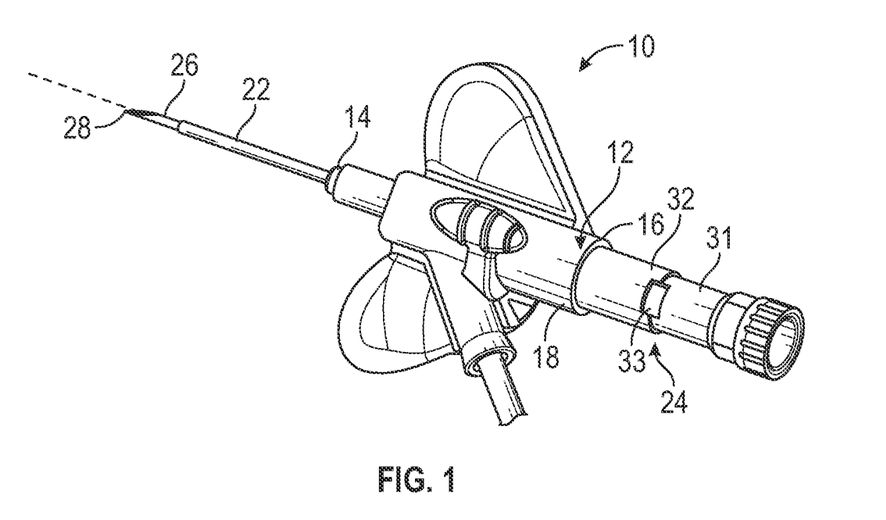
FIG. 1 is an upper perspective view of an example catheter system, according to some embodiments.

Referring now to FIG. 1, in some embodiments, a catheter system 10 may include a catheter adapter 12, which may include a distal end 14, a proximal end 16, and a wall 18 forming a lumen. In some embodiments, the catheter system 10 may include a catheter 22 extending distally from the distal end 14 of the catheter adapter 12. In some embodiments, the catheter 22 may be secured within the catheter adapter 12. In some embodiments, the catheter 22 may include a peripheral intravenous catheter ("PIVC"), a midline catheter, a peripherally inserted central catheter ("PICC"), or another suitable catheter.

In some embodiments, the catheter system 10 may include any suitable catheter adapter 12. In some embodiments, the catheter adapter 12 may include a side port in fluid communication with the lumen of the catheter adapter 12. In some embodiments, an extension tube may be integrated within the side port and may be part of an extension set. In some embodiments, the catheter adapter 12 may be straight or non-integrated and may not include the extension tube.

In some embodiments, the catheter system 10 may include a needle assembly 24 coupled to the catheter adapter 12. In some embodiments, the needle assembly 24 may include an introducer needle 26, which may include a distal tip 28 and a bump feature. In some embodiments, the introducer needle 26 may be constructed of metal, and the distal tip 28 may be sharp. In some embodiments, the distal tip 28 may be disposed distal to the catheter 22 in a first position, as illustrated, for example in FIG. 1. In some embodiments, the first position may correspond to an insertion position, ready for insertion into vasculature of a patient.

In some embodiments, a proximal end of the introducer needle 26 may be secured within a needle hub 31 of the needle assembly 24. In some embodiments, the needle assembly 24 may include a housing 32. In some embodiments, the needle hub 31 may include one or more grip features 33, which may facilitate movement of the needle hub in a proximal direction by a clinician to withdraw the introducer needle 26 from the vasculature of the patient and the catheter.

Figure 2A:
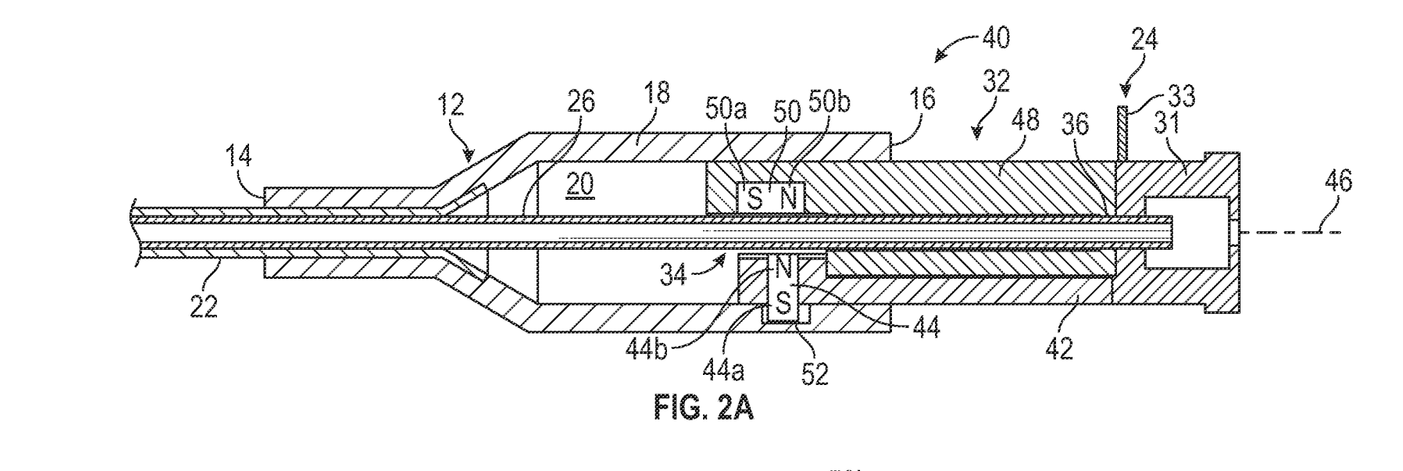
FIG. 2A is a cross-sectional view of a portion of another example catheter system, illustrating a distal tip of an example introducer needle in a first position, according to some embodiments.

Referring now to FIG. 2A, a catheter system 40 is illustrated, according to some embodiments. In some embodiments, the catheter system 40 may include or correspond to the catheter system 10 of FIG. 1. In some embodiments, the catheter system 40 may be similar or identical to the catheter system 10 of FIG. 1 in terms of one or more included components and/or operation.

In some embodiments, the needle hub 31 may be proximate the housing 32, as illustrated, for example in FIG. 2A. In some embodiments, the lumen 20 may extend through the distal end 14 and the proximal end 16. In some embodiments, the housing 32 of the needle assembly 24 may include a distal opening 34, a proximal opening 36, and a pathway 38 extending between the distal opening 34 and the proximal opening 36. In some embodiments, the pathway 38 may extend to the proximal opening 36. In some embodiments, a diameter of the proximal opening 36 may be less than an outer diameter of the bump feature 30 such that the bump feature 30 may not pass through the proximal opening 36. In some embodiments, the bump feature 30 may include any suitable feature having an increased outer diameter. In some embodiments, the introducer needle 26 may extend through the pathway 38.

In some embodiments, the housing 32 may include a first portion 42, which may include a magnet 44 extending there through. In some embodiments, the magnet 44 may include a first magnetic pole 44a and a second magnetic pole 44b. In some embodiments, the first magnetic pole 44a may be opposite the second magnetic pole 44b. For example, the first magnetic pole 44a may include a South Pole and the second magnetic pole 44b may include a North Pole or the first magnetic pole 44a may include a North Pole and the second magnetic pole 44b may include a South Pole. In some embodiments, the magnet 44 may include a permanent magnet. In some embodiments, the magnet 44 may be oriented generally perpendicular to a longitudinal axis 46 of the catheter system 40.

In some embodiments, the housing 32 may include a second portion 48, which may include another magnet 50. In some embodiments, the proximal opening 36 may be disposed in the second portion 48. In some embodiments, the distal opening 34 may be disposed between the first portion 42 and the second portion 48. In some embodiments, the other magnet 50 may include a first magnetic pole 50a and a second magnetic pole 50b. In some embodiments, the first magnetic pole 50a may be opposite the second magnetic pole 50b. For example, the first magnetic pole 50a may include a South Pole and the second magnetic pole 50b may include a North Pole or the first magnetic pole 50a may include a North Pole and the second magnetic pole 50b may include a South Pole. In some embodiments, the first magnetic pole 44a of the magnet 44 and the first magnetic pole 50a of the other magnet 50 may be a same pole and may be repelled by each other. In some embodiments, the second magnetic pole 44b of the magnet 44 and the second magnetic pole 50b of the other magnet 50 may be a same pole and repelled by each other.

In some embodiments, the other magnet 50 may include a permanent magnet. In some embodiments, the second magnetic pole 50b of the other magnet 50 may be proximal to the first magnetic pole 50a of the other magnet 50. In some embodiments, the other magnet 50 may be oriented generally parallel to a longitudinal axis of the catheter system 10. In some embodiments, the magnet 44 and/or the other magnet 50 may be proximate or in communication with the pathway 38, which may increase a magnetic force between the magnet 44 and the other magnet 50.

In some embodiments, the second magnetic pole 44b of the magnet 44 may be generally aligned with and repelled by the second magnetic pole 50b of the other magnet 50, as illustrated, for example, in FIG. 2A. In some embodiments, the introducer needle 26 may be disposed between the second magnetic pole 44b of the magnet 44 and the second magnetic pole 50b of the other magnet 50. In some embodiments, the magnetic repulsion between the second magnetic pole 44b of the magnet 44 and the second magnetic pole 50b of the other magnet 50 may reduce a friction-based drag force on the introducer needle 26 as the introducer needle 26 is proximally withdrawn.

In some embodiments, due to the magnetic repulsion between the second magnetic pole 44b of the magnet 44 and the second magnetic pole 50b of the other magnet 50, the second magnetic pole 44b of the magnet 44 and/or the second magnetic pole 50b of the other magnet 50 may be spaced apart from an outer surface of the introducer needle 26, which may reduce the friction-based drag force on the introducer needle 26 as the introducer needle 26 is proximally withdrawn. In some embodiments, the magnet 44 and/or the other magnet 50 may lightly contact the introducer needle 26. In some embodiments, the introducer needle 26 may be spaced apart from all or a portion of the housing 32 forming the pathway 38, which may reduce the friction-based drag force on the introducer needle 26 as the introducer needle 26 is proximally withdrawn.

In some embodiments, an inner surface of the wall 18 of the catheter adapter 12 may include a slot 52, which may include a hole 152 extending through the first portion 42 or a groove. In some embodiments, the first magnetic pole 44a of the magnet 44 may be disposed within the slot 52, which may couple the needle assembly 24 to the catheter adapter 12. In some embodiments, when the catheter adapter 12 is coupled to the needle assembly 24 via the other magnet 50 disposed in the slot 52, a magnetic repelling force between the magnet 44 and the other magnet 50 may be at a high or peak value, which may secure the catheter adapter 12 and the needle assembly 24 together and may simultaneously reduce the friction-based drag force.

Figure 2B:
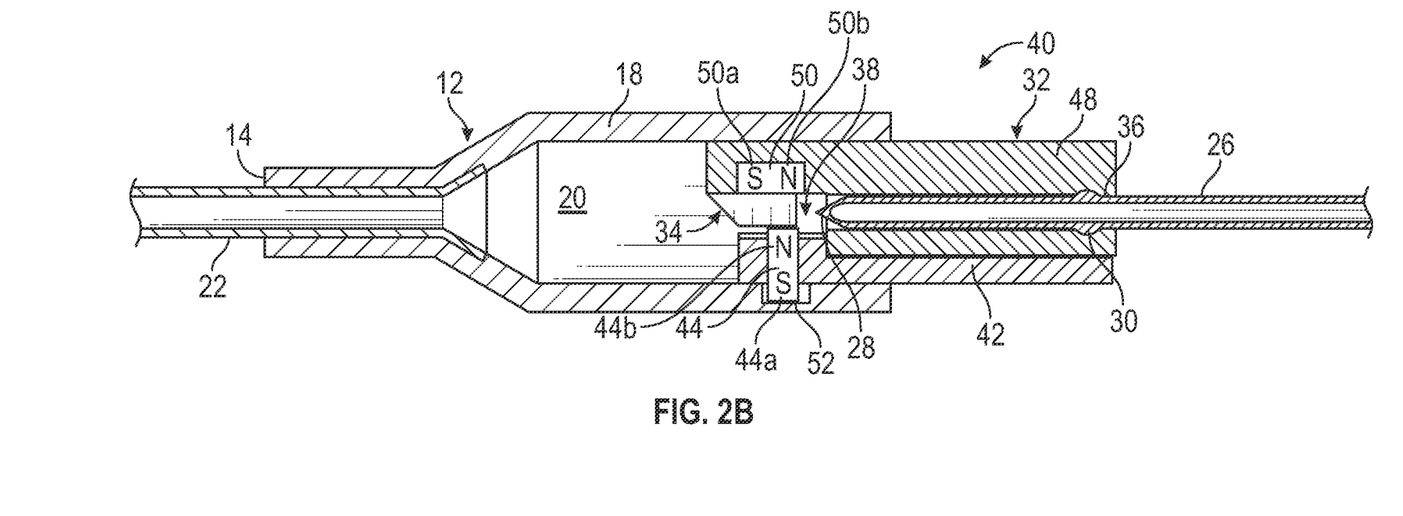
FIG. 2B is a cross-sectional view of a portion of the catheter system of FIG. 2A, illustrating the distal tip of the introducer needle in a second position, according to some embodiments.

Referring now to FIG. 2B, in some embodiments, the distal tip 28 of the introducer needle 26 may be configured to be withdrawn proximally from the first position to a second position in which the bump feature 30 contacts the proximal opening 36. In some embodiments, the bump feature 30 may be prevented from passing through the proximal opening 36 due to the outer diameter of the bump feature 30.

Figure 2C:
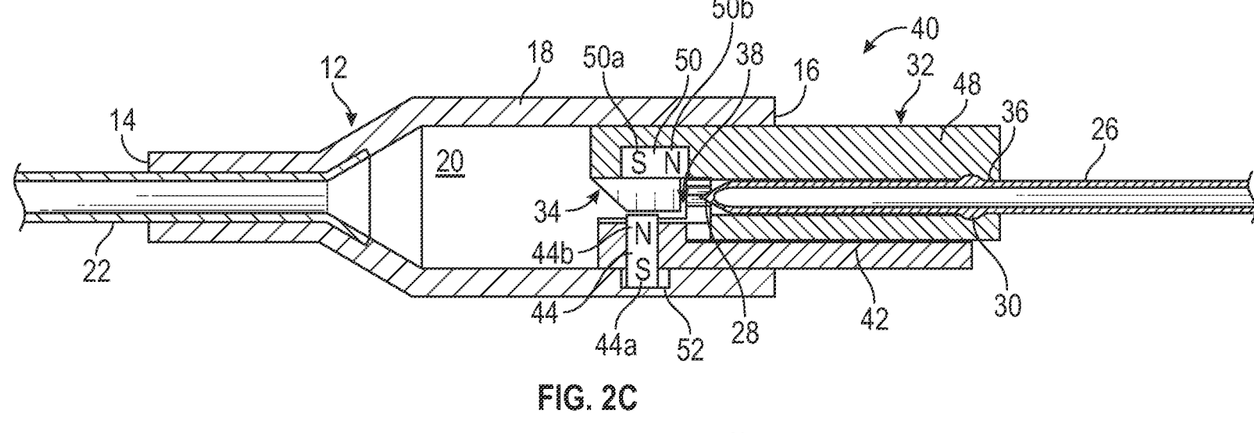
FIG. 2C is a cross-sectional view of a portion of the catheter system of FIG. 2A, illustrating the distal tip of the introducer needle in a third position, according to some embodiments.
Figure 2D:
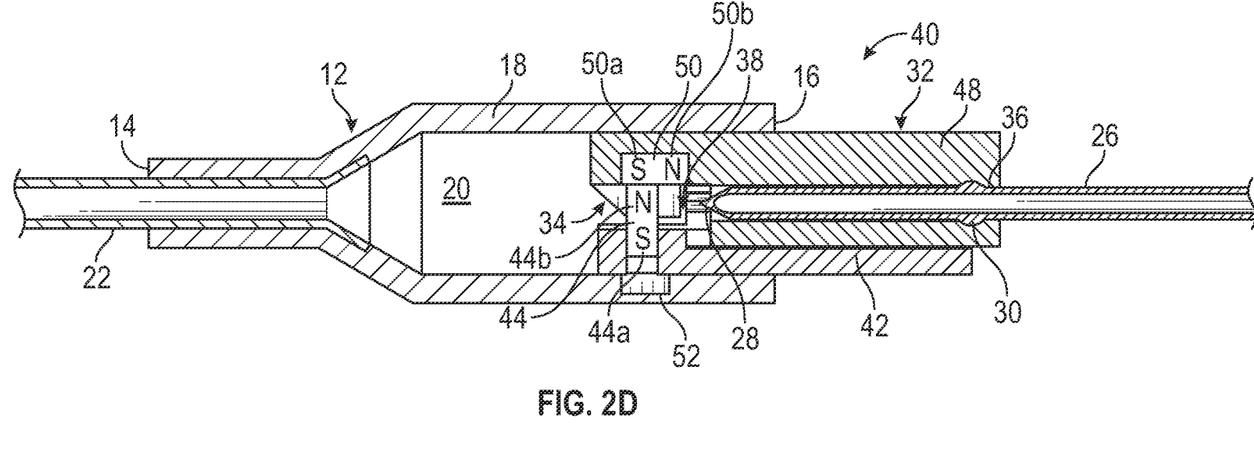
FIG. 2D is a cross-sectional view of a portion of the catheter system of FIG. 2A, illustrating the catheter system in a shielded position in response to proximal withdrawal of the distal tip of the introducer needle from the second position to the third position, according to some embodiments.

Referring now to FIGS. 2C-2D, in some embodiments, the distal tip 28 of the introducer needle 26 may be configured to be withdrawn proximally from the second position to a third position. In some embodiments, in response to withdrawing the distal tip 28 of the introducer needle 26 proximally from the second position to the third position, the second portion 48 may slide proximally with respect to the first portion 42, and the second magnetic pole 44b of the magnet 44 may be generally aligned with and attracted to the first magnetic pole 50a of the other magnet 50 such that the magnet 44 moves inwardly towards the other magnet 50. In some embodiments, in response to the magnet 44 moving inwardly towards the other magnet 50, the magnet 44 may block the distal opening 34 and/or prevent blood from leaking out the distal opening 34. In some embodiments, when the distal tip 28 is disposed in the third position, a magnetic attraction force between the magnet 44 and the other magnet 50 may be at a high or peak value, which may facilitate securement of the distal tip 28 within the housing 32.

In some embodiments, the catheter system 40 may be locked when the distal tip 28 is in the third position such that the distal tip 28 is prevented from exposure and bypassing the magnet 44. In some embodiments, the catheter system 40 may be locked via geometry of one or more components of the catheter system 40, such as, for example, the magnet 44 and/or the other magnet 50. In some embodiments, the catheter system 40 may be locked due to the inward motion of the magnet 44, and the strength of the magnetic attraction force between the magnet 44 and the other magnet 50. In some embodiments, the catheter system 40 may include a lube or coating, which may reduce undesirable forces within the catheter system 40.

In some embodiments, the magnet 44 may shield the distal tip 28 within the housing 32 when the distal tip 28 is disposed in the third position and may also act as a coupling component configured to couple the needle assembly 24 to the catheter adapter 12 when the distal tip 28 is in the first position and/or the second position. In some embodiments, in response to withdrawing the distal tip 28 of the introducer needle 26 proximally from the second position to the third position, the second magnetic pole 44b of the magnet 44 may be generally aligned with and attracted to the first magnetic pole 50a of the other magnet 50 such that the magnet 44 moves inwardly towards the other magnet 50 and is removed from the slot 52.

Figure 2E:
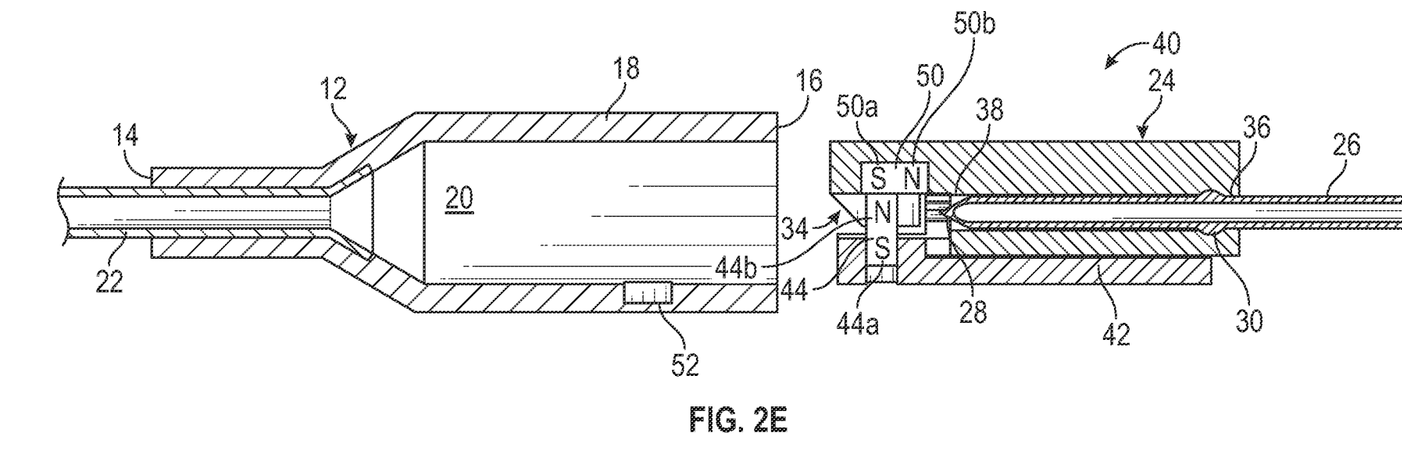
FIG. 2E is a cross-sectional view of a portion of the catheter system of FIG. 2A, illustrating an example needle assembly of the catheter system of FIG. 2A uncoupled and removed from an example catheter adapter, according to some embodiments.
Figure 2F:
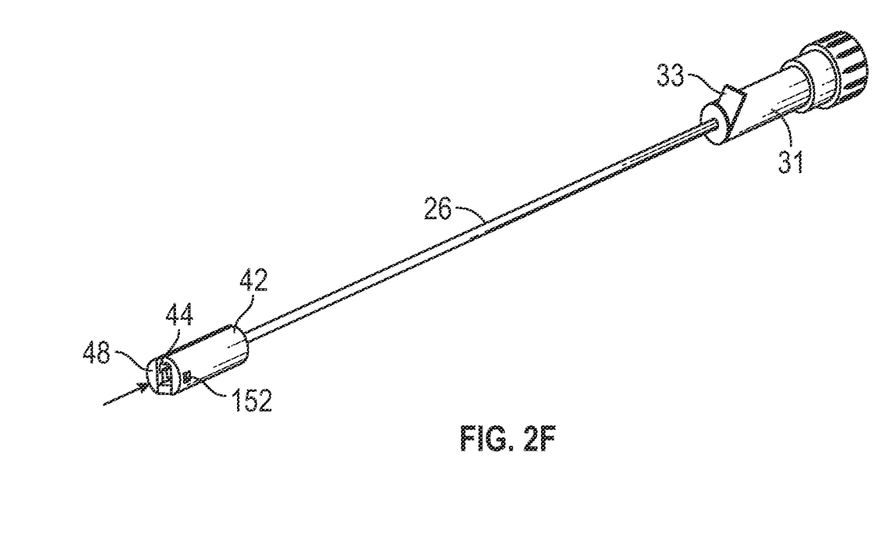
FIG. 2F is an upper perspective view of the needle assembly of the catheter system of FIG. 2A removed from the catheter adapter, according to some embodiments.

Referring now to FIGS. 2E-2F, in some embodiments, in response to the other magnet 50 being removed from the slot 52, the catheter adapter 12 and the needle assembly 24 may be uncoupled and/or the needle assembly 24 may be removed from the catheter adapter 12.

Figure 3A:
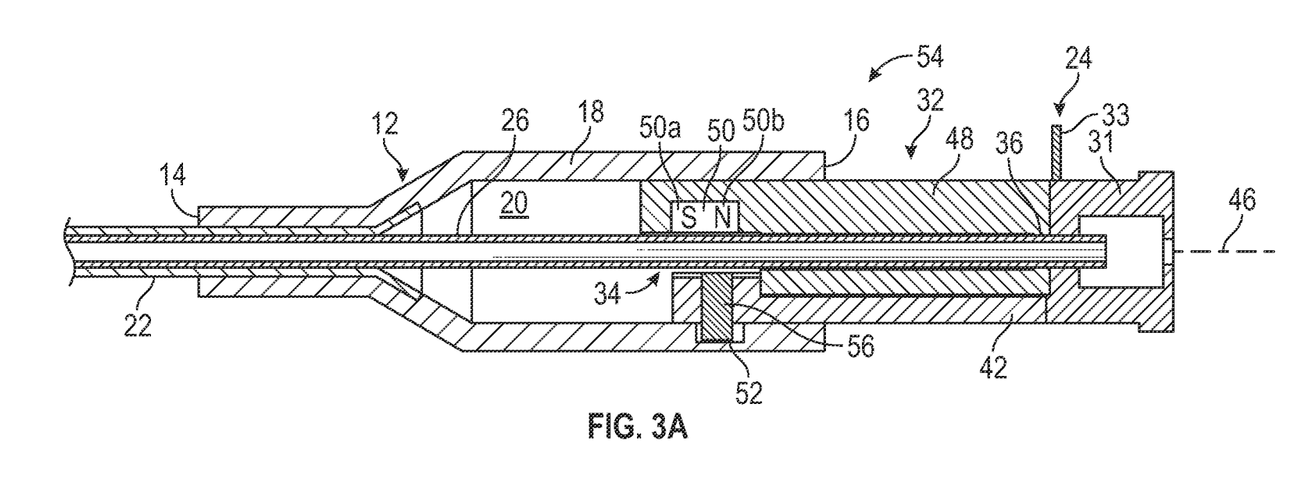
FIG. 3A is a cross-sectional view of a portion of another catheter system, illustrating the distal tip of the introducer needle in the first position, according to some embodiments.

Referring now to FIG. 3A, a catheter system 54 is illustrated, according to some embodiments. In some embodiments, the catheter system 54 may include or correspond to the catheter system 10 of FIG. 1 and/or the catheter system 40 of FIG. 2. In some embodiments, the catheter system 40 may be similar or identical to the catheter system 10 of FIG. 1 and/or the catheter system 40 of FIG. 2 in terms of one or more included components and/or operation.

In some embodiments, the magnet 44 of the catheter system 40 of FIG. 2 may be replaced with a temporary magnet 56 in the catheter system 54. In these and other embodiments, the first portion 42 and the second portion 48 may be integrally formed and may not slide with respect to each other. In some embodiments, the first portion 42 and the second portion 48 may be monolithically formed as a single unit. In some embodiments, the temporary magnet 56 may include steel, iron, metal, or another suitable material. In some embodiments, the introducer needle 26 may be disposed between the other magnet 50 and the temporary magnet 56.

In some embodiments, the other magnet 50 may include a permanent magnet, and the temporary magnet 56 may be attracted to the permanent magnet. In some embodiments, the temporary magnet 56 may contact and/or press lightly on the introducer needle 26 when the distal tip 28 is in the first position due to the attraction between the temporary magnet 56 and the other magnet 50. In some embodiments, the other magnet 50 may be spaced apart from the introducer needle 26 when the distal tip 28 is in the first position, which may reduce the friction-based drag force on the introducer needle 26 as the introducer needle 26 is withdrawn. In some embodiments, the other magnet 50 may contact and/or press lightly on the introducer needle 26 when the distal tip 28 is in the first position. In some embodiments, the temporary magnet 56 may be disposed within the slot 52, which may couple and secure the needle assembly 24 to the catheter adapter 12. In some embodiments, a magnetic attraction force between the temporary magnet 56 and the other magnet 50 may be constant.

Figure 3B:
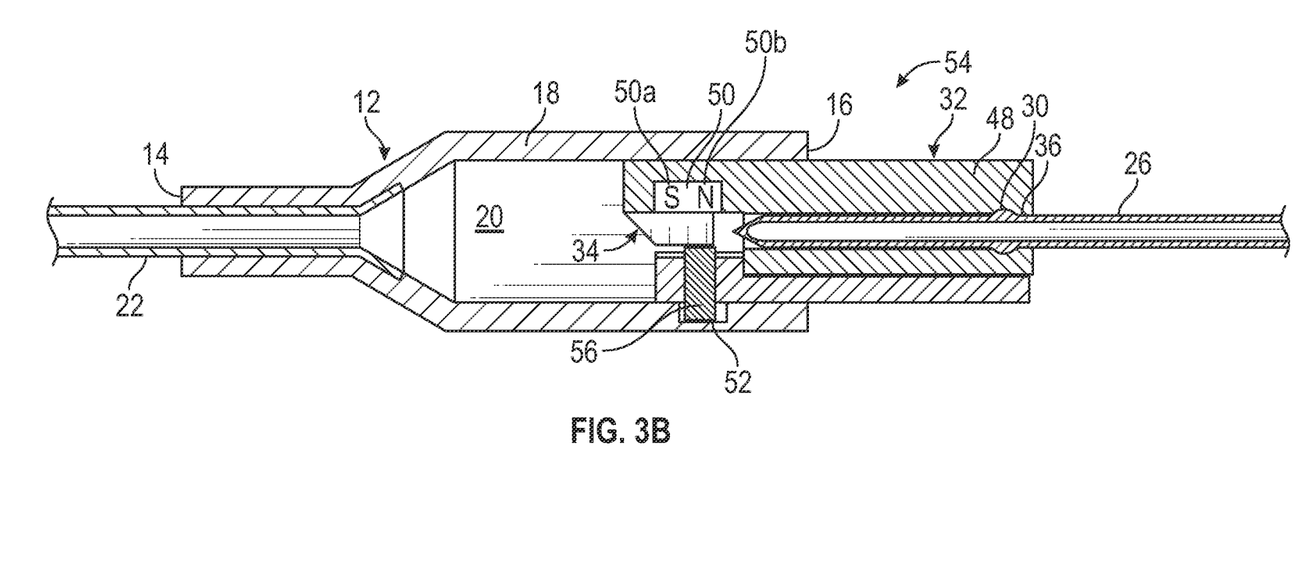
FIG. 3B is a cross-sectional view of a portion of the catheter system of FIG. 3A, illustrating the distal tip of the introducer needle in the second position, according to some embodiments.

Referring now to FIG. 3B, in some embodiments, the distal tip 28 of the introducer needle 26 may be configured to be withdrawn proximally from the first position to the second position. In some embodiments, in response to withdrawing the distal tip 28 of the introducer needle 26 proximally from the first position to the second position, the bump feature 30 may contact the proximal opening 36 of the housing 32 and the distal tip 28 may be disposed proximal to the temporary magnet 56 and the other magnet 50.

Figure 3C:
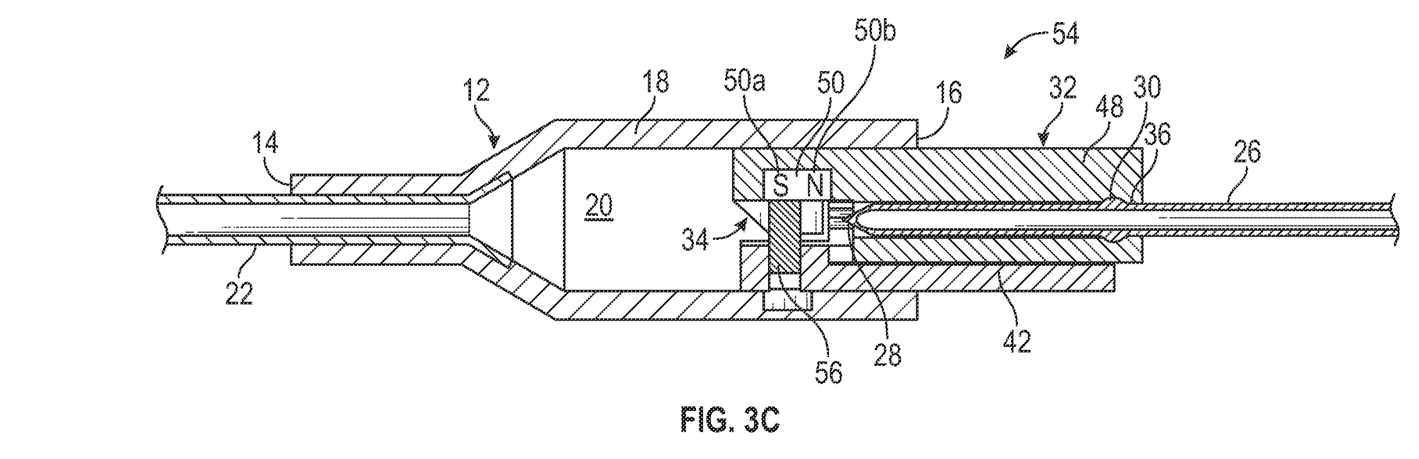
FIG. 3C is a cross-sectional view of a portion of the catheter system of FIG. 3A, illustrating the catheter system in a shielded position in response to proximal withdrawal of the distal tip of the introducer needle from the first position to the second position, according to some embodiments, according to some embodiments.

Referring now to FIG. 3C, in some embodiments, in response to withdrawing the distal tip 28 of the introducer needle 26 proximally from the first position to the second position, the temporary magnet 56 may move inwardly towards the other magnet 50 to block the distal opening 34 and/or prevent blood from leaking out the distal opening 34. In some embodiments, in response to withdrawing the distal tip 28 of the introducer needle 26 proximally from the first position to the second position, the temporary magnet 56 may move inwardly towards the other magnet 50 and may be removed from the slot 52.

In some embodiments, the catheter system 54 may be locked when the distal tip 28 is in the second position such that the distal tip 28 is prevented from exposure and bypassing the temporary magnet 56. In some embodiments, the catheter system 40 may be locked via geometry of one or more components of the catheter system 54, such as, for example, the temporary magnet 56 and/or the other magnet 50. In some embodiments, the catheter system 54 may be locked due to the inward motion of the temporary magnet 56, and the strength of the magnetic attraction force between the temporary magnet 56 and the other magnet 50. In some embodiments, the catheter system 54 may include a lube or coating, which may reduce undesirable forces within the catheter system 54.

Figure 3D:
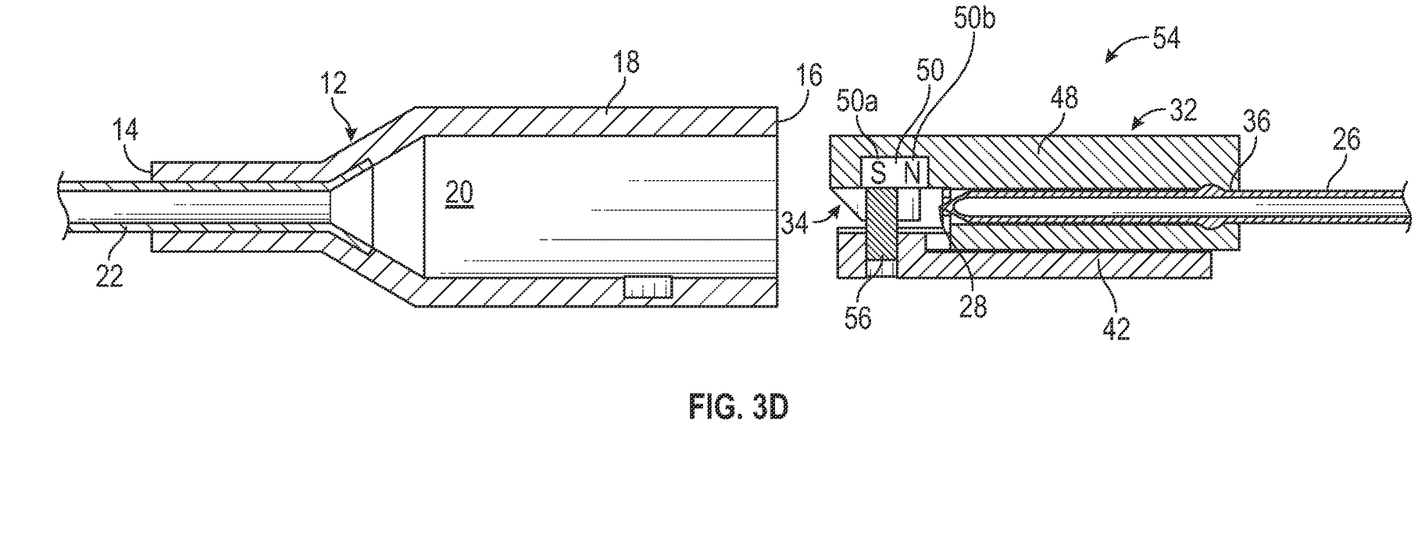
FIG. 3D is a cross-sectional view of a portion of the catheter system of FIG. 3A, illustrating an example needle assembly of the catheter system of FIG. 3A uncoupled and removed from an example catheter adapter, according to some embodiments.

Referring now to FIG. 3D, in some embodiments, in response to the temporary magnet 56 being removed from the slot 52, the catheter adapter 12 and the needle assembly 24 may be uncoupled and/or the needle assembly 24 may be removed from the catheter adapter 12.

Figure 3E:
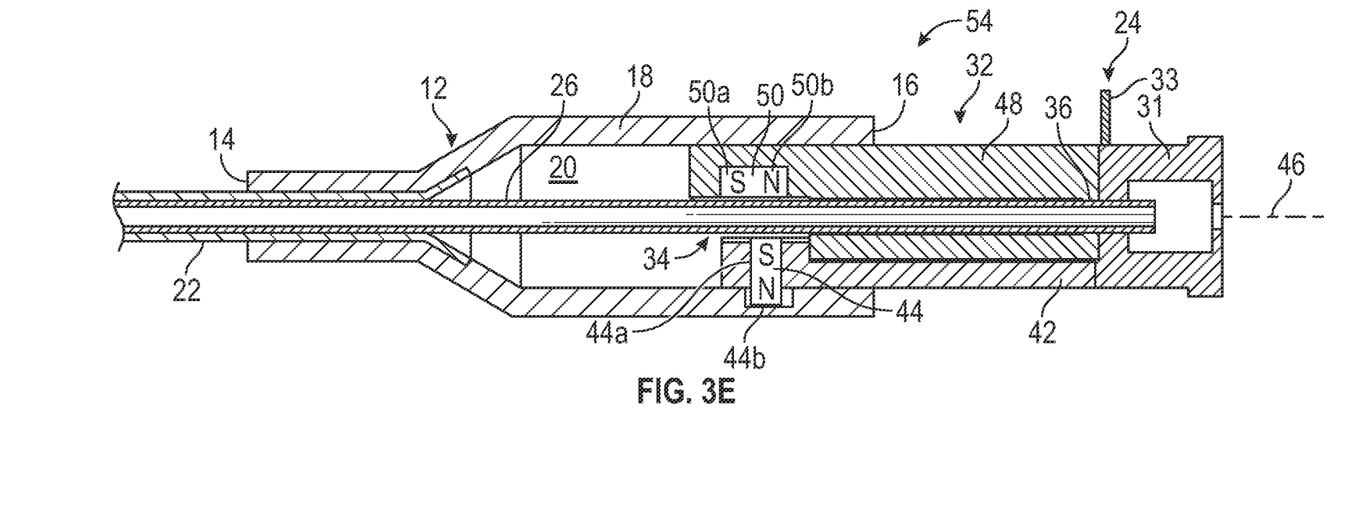
FIG. 3E is a cross-sectional view of a portion of the catheter system of FIG. 3A, illustrating the distal tip of the introducer needle in the first position, according to some embodiments.

Referring now to FIG. 3E, the temporary magnet 56 may be replaced with the magnet 44, which may be oriented such that the first magnetic pole 44a is aligned with the second magnetic pole 50b when the distal tip 28 is in the first position and/or the second position. In these and other embodiments, the first portion 42 and the second portion 48 may be integrally formed and may not slide with respect to each other. In some embodiments, the first portion 42 and the second portion 48 may be monolithically formed as a single unit.

In some embodiments, the magnet 44 may contact and/or press lightly on the introducer needle 26 when the distal tip 28 is in the first position due to the attraction between the magnet 44 and the other magnet 50. In some embodiments, the other magnet 50 may be spaced apart from the introducer needle 26 when the distal tip 28 is in the first position, which may reduce the friction-based drag force on the introducer needle 26 as the introducer needle 26 is withdrawn. In some embodiments, the other magnet 50 may contact and/or press lightly on the introducer needle 26 when the distal tip 28 is in the first position. In some embodiments, the magnet 44 may be disposed within the slot 52, which may couple and secure the needle assembly 24 to the catheter adapter 12.

In some embodiments, in response to withdrawing the distal tip 28 of the introducer needle 26 proximally from the first position to the second position, the magnet 44 may move inwardly towards the other magnet 50 to block the distal opening 34 and/or prevent blood from leaking out the distal opening 34. In some embodiments, in response to withdrawing the distal tip 28 of the introducer needle 26 proximally from the first position to the second position, the magnet 44 may move inwardly towards the other magnet 50 and may be removed from the slot 52.

Figure 4A:
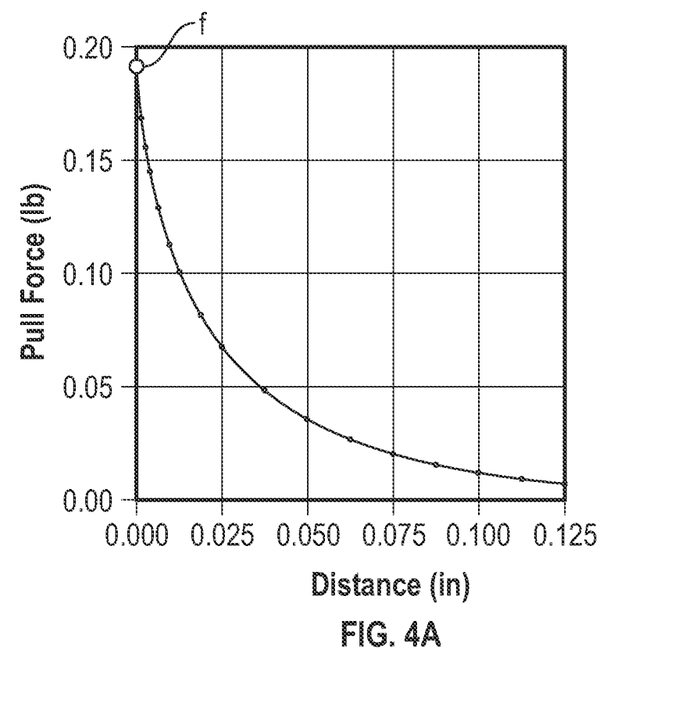
FIG. 4A is a graph illustrating withdrawal distance of the introducer needle versus pull force, according to some embodiments.

Referring now to FIG. 4A, a graph of remaining withdrawal distance of the distal tip 28 versus pull force is illustrated, according to some embodiments. In some embodiments, the graph of FIG. 4A may correspond to the catheter system 40. As illustrated in the graph, in some embodiments, a highest attraction force f between the magnet 44 and the other magnet 50 or between the other magnet 50 and the temporary magnet 56 may be achieved in the third position, when the distal tip 28 may be shielded within the housing 32. The remaining withdrawal distance and pull force values of the graph of FIG. 4A are meant to be examples for illustration purposes and are not limiting.

Figure 4B:
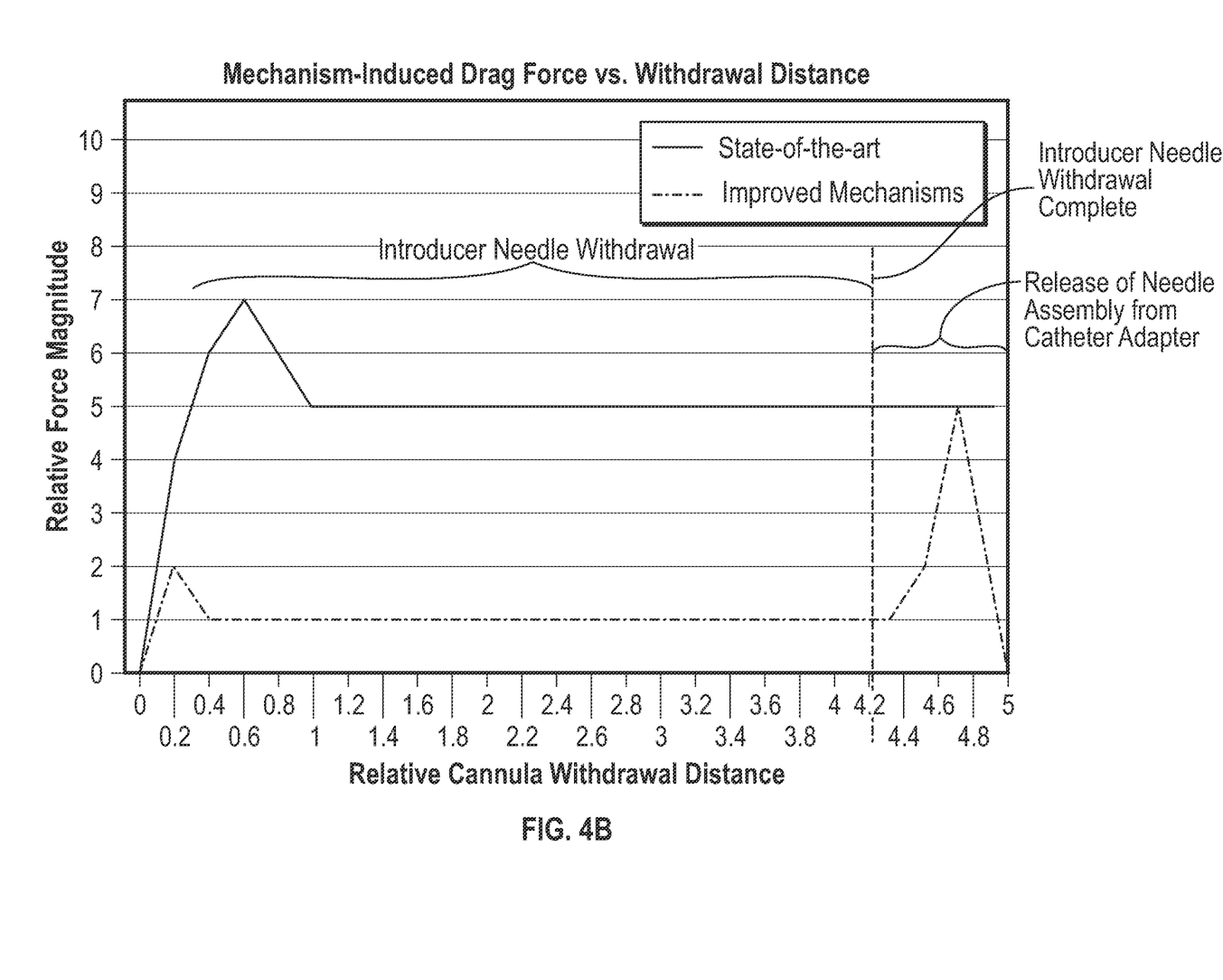
FIG. 4B is a graph illustrating mechanism-induced friction-based drag force versus withdrawal distance, according to some embodiments.

Referring now to FIG. 4B, the catheter system 40 and/or the catheter system 54 may be configured to reduce or eliminate friction-induced drag force on the introducer needle 26 during withdrawal of the introducer needle 26 from the patient and a catheter assembly, which may include the catheter adapter 12 and the catheter 22. In some embodiments, the catheter system 40 and/or the catheter system 54 may be configured to reduce or eliminate friction-induced drag force on the introducer needle 26 during final stages of withdrawal of the introducer needle 26 from the patient and the catheter assembly. In some embodiments, the graph of FIG. 4B may correspond to the catheter system 40 and/or the catheter system 54. In some embodiments, the reduced friction-induced drag may reduce a likelihood of the clinician accidentally dislodging the catheter 22 from an insertion site and the vasculature. The distance and relative force magnitude values of FIG. 4B are meant to be examples for illustration purposes and are not limiting.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention. It should be understood that the embodiments may be combined.

We claim:
1. A catheter system, comprising:
   a catheter adapter, comprising a distal end, a proximal end, and a wall forming a lumen;
   a catheter extending distally from the distal end of the catheter adapter; and a needle assembly coupled to the catheter adapter, the needle assembly comprising:
an introducer needle, comprising a distal tip and a bump feature, wherein the distal tip is disposed distal to the catheter in a first position; and
a housing, comprising:
a distal opening;
a proximal opening, wherein a diameter of the proximal opening is less than an outer diameter of the bump feature;
a pathway extending between the distal opening and the proximal opening, wherein the introducer needle extends through the pathway; and
a first portion, comprising a magnet extending through the first portion, wherein the magnet comprises a first magnetic pole and a second magnetic pole;
a second portion comprising another magnet, wherein the other magnet comprises a first magnetic pole and a second magnetic pole, wherein the second magnetic pole of the other magnet is proximal to the first magnetic pole of the other magnet, wherein the second magnetic pole of the magnet is generally aligned with and repelled by the second magnetic pole of the other magnet, wherein the introducer needle is disposed between the second magnetic pole of the magnet and the second magnetic pole of the other magnet,
wherein the distal tip of the introducer needle is configured to be withdrawn proximally from the first position to a second position in which the bump feature contacts the proximal opening and proximally from the second position to a third position, wherein in response to withdrawing the distal tip of the introducer needle proximally from the second position to the third position, the second portion slides proximally with respect to the first portion and the second magnetic pole of the magnet is aligned with and attracted to the first magnetic pole of the other magnet such that the magnet moves inwardly towards the other magnet.

2. The catheter system of claim 1, wherein in response to withdrawing the distal tip of the introducer needle proximally from the second position to the third position, the second magnetic pole of the magnet is aligned with and attracted to the first magnetic pole of the other magnet such that the magnet moves inwardly towards the other magnet to block the distal opening.

3. The catheter system of claim 1, wherein the wall of the catheter adapter comprises a slot, wherein the first magnetic pole of the magnet is disposed within the slot, wherein in response to withdrawing the distal tip of the introducer needle proximally from the second position to the third position, the second magnetic pole of the magnet is aligned with and attracted to the first magnetic pole of the other magnet such that the magnet moves inwardly towards the other magnet and is removed from the slot.

4. The catheter system of claim 3, wherein in response to the magnet being removed from the slot, the catheter adapter and the needle assembly are uncoupled.

5. The catheter system of claim 1, wherein the second magnetic pole of the magnet and the second magnetic pole of the other magnet are spaced apart from an outer surface of the introducer needle.

6. The catheter system of claim 1, wherein the magnet is oriented generally perpendicular to a longitudinal axis of the catheter system.

7. The catheter system of claim 1, wherein the other magnet is oriented generally parallel to a longitudinal axis of the catheter system.

8. The catheter system of claim 1, wherein the magnet is proximate the pathway.

9. The catheter system of claim 1, wherein the other magnet is proximate the pathway.

10. The catheter system of claim 1, wherein the magnet and the other magnet are permanent magnets.

11. The catheter system of claim 1, wherein the proximal end of the introducer needle is secured within a needle hub.

12. A catheter system, comprising:
a catheter adapter, comprising a distal end, a proximal end, and a wall forming a lumen;
a catheter extending distally from the distal end of the catheter adapter; and
a needle assembly coupled to the catheter adapter, the needle assembly comprising:
an introducer needle, comprising a distal tip and a bump feature, wherein the distal tip is disposed distal to the catheter in a first position; and
a housing, comprising:
a distal opening;
a proximal opening, wherein a diameter of the proximal opening is less than an outer diameter of the bump feature;
a pathway extending between the distal opening and the proximal opening, wherein the introducer needle extends through the pathway;
a first portion comprising a temporary magnet extending through the first portion; and
a second portion comprising a permanent magnet secured within the second portion, wherein the permanent magnet comprises a first magnetic pole and a second magnetic pole, wherein the introducer needle is disposed between the temporary magnet and the permanent magnet,
wherein the distal tip of the introducer needle is configured to be withdrawn proximally from the first position to a second position in which the distal tip is disposed proximal to the temporary magnet and the permanent magnet, wherein in response to withdrawing the distal tip of the introducer needle proximally from the first position to the second position, the bump feature contacts the proximal opening to cause the second portion to move proximally relative to the first portion, the proximal movement of the second portion relative to the first portion causing the temporary magnet to move inwardly towards the permanent magnet.

13. The catheter system of claim 12, wherein the proximal movement of the second portion relative to the first portion causes the temporary magnet to align with the first magnetic pole.

14. The catheter system of claim 12, wherein the wall of the catheter adapter comprises a slot, wherein the temporary magnet is disposed within the slot, wherein in response to withdrawing the distal tip of the introducer needle proximally from the first position to the second position, the temporary magnet moves inwardly towards the permanent magnet and is removed from the slot.

15. The catheter system of claim 14, wherein in response to the temporary magnet being removed from the slot, the catheter adapter and the needle assembly are uncoupled.

16. The catheter system of claim 12, wherein the temporary magnet is proximate the pathway.

17. The catheter system of claim 12, wherein the permanent magnet is proximate the pathway.

18. The catheter system of claim 12, wherein the temporary magnet comprises steel.

19. The catheter system of claim 12, wherein the permanent magnet is spaced apart from the introducer needle, wherein the temporary magnet contacts the introducer needle.

20. The catheter system of claim 12, wherein the proximal end of the introducer needle is secured within a needle hub.

* * * * *